(12) United States Patent
Gboluaje

(10) Patent No.: US 8,711,358 B1
(45) Date of Patent: Apr. 29, 2014

(54) SUBMERSIBLE REMOTE SMOKE SENSOR

(71) Applicant: Temitayo Gboluaje, Silver Spring, MD (US)

(72) Inventor: Temitayo Gboluaje, Silver Spring, MD (US)

(73) Assignee: Temitayo Gboluaje, Silver Spring, MD (US)

( * ) Notice: Subject to any disclaimer, the term of this patent is extended or adjusted under 35 U.S.C. 154(b) by 11 days.

(21) Appl. No.: 13/775,224

(22) Filed: Feb. 24, 2013

(51) Int. Cl.
*G01N 21/53* (2006.01)
*G08B 17/10* (2006.01)

(52) U.S. Cl.
CPC ................. *G01N 21/53* (2013.01); *G08B 17/10* (2013.01)
USPC ............ 356/438; 356/437; 430/630; 430/628

(58) Field of Classification Search
CPC ................................ G01N 21/53; G08B 17/10
USPC .......... 356/432–438, 336–338; 250/573, 574; 430/630, 629, 628, 632, 577; 435/7.1
See application file for complete search history.

(56) References Cited

U.S. PATENT DOCUMENTS

| | | | | |
|---|---|---|---|---|
| 3,982,130 | A * | 9/1976 | Trumble | 250/373 |
| 5,502,434 | A * | 3/1996 | Minowa et al. | 340/630 |
| 6,107,925 | A * | 8/2000 | Wong | 340/628 |
| 6,545,608 | B1 * | 4/2003 | Kaufman | 340/577 |
| 7,167,099 | B2 * | 1/2007 | Kadwell et al. | 340/630 |
| 7,301,641 | B1 * | 11/2007 | Overby et al. | 356/438 |
| 2002/0117325 | A1 * | 8/2002 | Mennone et al. | 174/121 A |
| 2004/0063154 | A1 * | 4/2004 | Booth et al. | 435/7.1 |
| 2010/0267361 | A1 * | 10/2010 | Sullivan | 455/404.2 |
| 2012/0140233 | A1 * | 6/2012 | Rockwell et al. | 356/445 |

* cited by examiner

*Primary Examiner* — Sang Nguyen

(57) ABSTRACT

A device that detects smoke, both indoor and outdoor; especially applicable in areas prone to sustained water flooding. It can be used in underground locations susceptible to water ingress so it can be submersed in up to 6 feet of water for up to 24 hours. Usable in applications that requires NEMA 6P or IP68 level of water protection.

1 Claim, 7 Drawing Sheets

17

SUBMERSIBLE REMOTE SMOKE SENSOR

FIELD OF THE INVENTION

The present invention relates to the field of condition monitoring within a defined space. Specifically, the present invention provides a solution for monitoring smoke or fire in any location. More specifically in underground locations that can retain water up to the level that submerses the device in water for a prolonged period of time.

BACKGROUND OF THE INVENTION

Present day smoke detectors are not suitable for use in areas with possibility of water ingress or in areas susceptive to flooding. Most smoke detectors use ionization to detect the presence of smoke, therefore the compartment that analysis the air for smoke is exposed and susceptive to water ingress. The smoke detectors that utilize beam projection are kept in enclosures that are prone to water ingress.

Needless to say a technology that utilizes beam projection for smoke detection starts the process for a solution of smoke detector that can withstand water. The challenge is then how to house the beam projected smoke detector in such a way that it prevents water ingress, even in prolong situations while preserving the ability of the detector to sense different levels of smoke intrusions.

Smoke detection utilizing beam projection in a water submersible material is hence desirable. Attempts to satisfy the need have been made by enclosing a beam detector in a NEMA 6P enclosure.

BRIEF SUMMARY OF THE INVENTION

Accordingly, it is the goal of the present invention to provide a smoke detector, which overcomes the challenges associated with the prior art as described in parts discussed above.

Hence, in the first aspect is a provision for water submersion of a beam detector through the use of a NEMA 6P enclosure. The detector is fitted into an enclosure which prevents water ingress in any possible water related events like rain and flooding.

The alarm cables from the beam detector routes through a NEMA 6P cord grip that prevents water ingress through the cable entry into the enclosure. Four screws on the enclosure ensure the enclosure is sealed from water ingress and certifies the enclosure meets a NEMA 6P rating.

In summary, the invention utilizes a beam directed smoke detector in conjunction with a NEMA 6P enclosure, along with a NEMA 6P cord grip to provide a solution that can allow for smoke and fire detection in areas susceptive to flooding and water ingress.

BRIEF DESCRIPTION OF THE DRAWING

After describing the invention with words, references will now be made to accompany drawings that illustrate the invention and it should be noted that the drawings are not to scale and only for illustration only.

DETAILED DESCRIPTION OF THE INVENTION

The present invention will now be described in reference to the accompanying drawings. It should be noted that the embodiments of the invention represented in this document is just one of the various ways the invention can be represented and it should not be misconstrued as the only possible way of representing the invention. Similar numbers on the drawings refers to the same elements.

Figure 1:
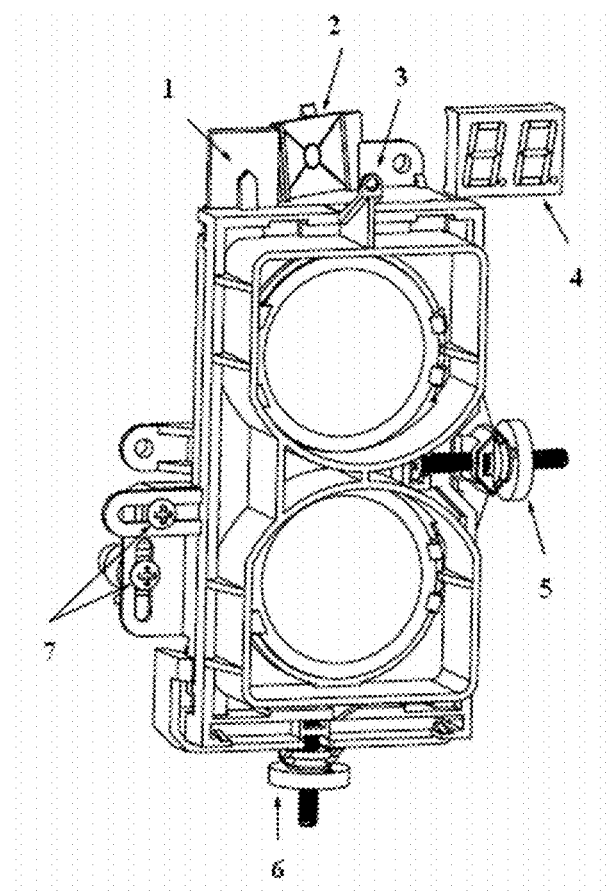
FIG. 1 shows the laser beam transmitter and laser beam detector which generates the laser beam and detects its reflection in the present invention

FIG. 1 also represented as element 1 shows the laser beam detector which is the unit that creates a laser beam of light that is constantly generated to detect presence of smoke in air. FIG. 1 shines the laser beam on FIG. 2 which reflects the entire laser beam back to FIG. 1 if there is no smoke, flame or any kind of obstruction between the two. Otherwise, FIG. 2 reflects a fraction to none of the beam sent by FIG. 1 therefore activating an alarm depending on the alarm set point for the fraction of the laser beam that must be received by FIG. 1 to deem the environment has smoke or fire.

Figure 2:
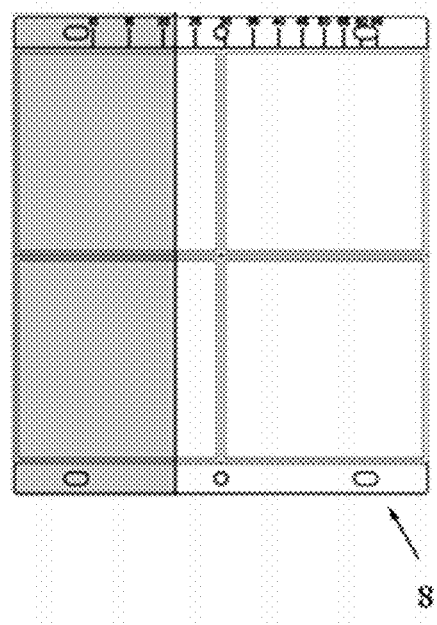
FIG. 2 shows a reflecting panel which reflects the beam in the present invention

In FIG. 1, 2 is the adjustment mirror that is used to align FIG. 1 and FIG. 2 during installation and 3 helps in determining when an alignment has been reached while 5, 6 and 7 are adjustment knobs used to reach alignment. Element 4 is a two seven segment display used for communicating settings on the beam detector.

Figure 3:
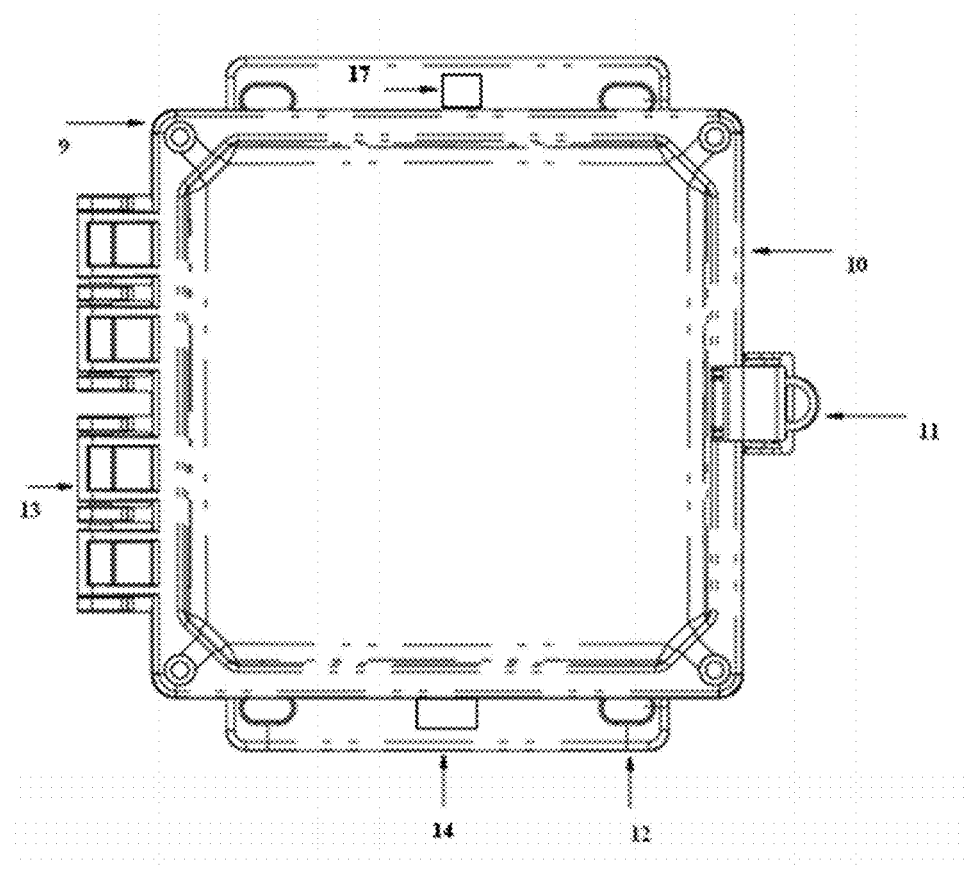
FIG. 3 shows the front view of the NEMA 6P enclosure that houses the beam detector in the present invention
Figure 5:
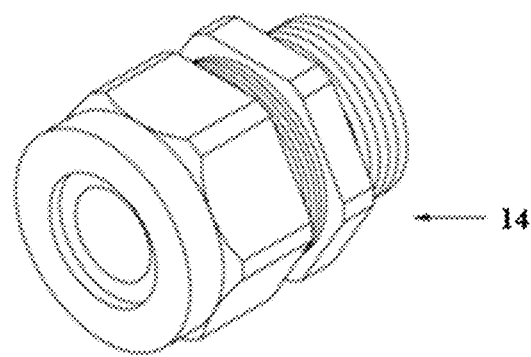
FIG. 5 shows a water tight cord grip that allows the alarm cable from the beam detector to pass through the enclosure without making the enclosure vulnerable to water ingress

FIG. 3 is the NEMA 6P enclosure that houses FIG. 1. element 14 on FIG. 3 is FIG. 5 which is the water tight cord grip that allows alarm cable from FIG. 1 to reach an alarm station (not shown on any of the drawings) where the alarm is received remotely in event of fire or detection of smoke. Element 17 is the local alarm switch used for resetting the device locally after detection of smoke. FIG. 3 and FIG. 5 create the water tight barrier between FIG. 1 and any environment the system is installed in. FIG. 5 allows an alarm and alarm reset cable to extend from FIG. 1 to the outer part of FIG. 3.

Figure 4:
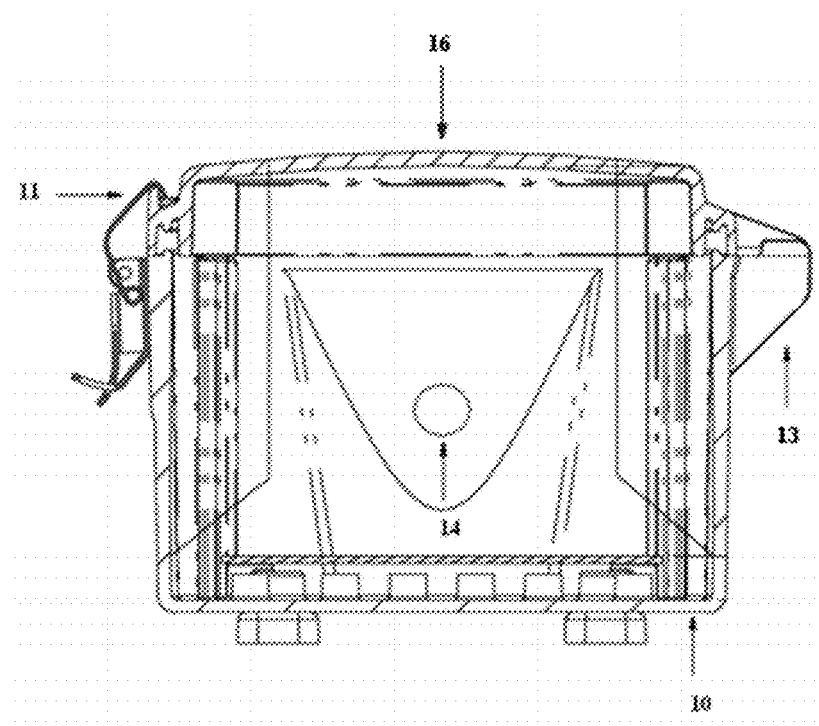
FIG. 4 shows the bottom view of the NEMA 6P enclosure and the transparent lid.
Figure 6:
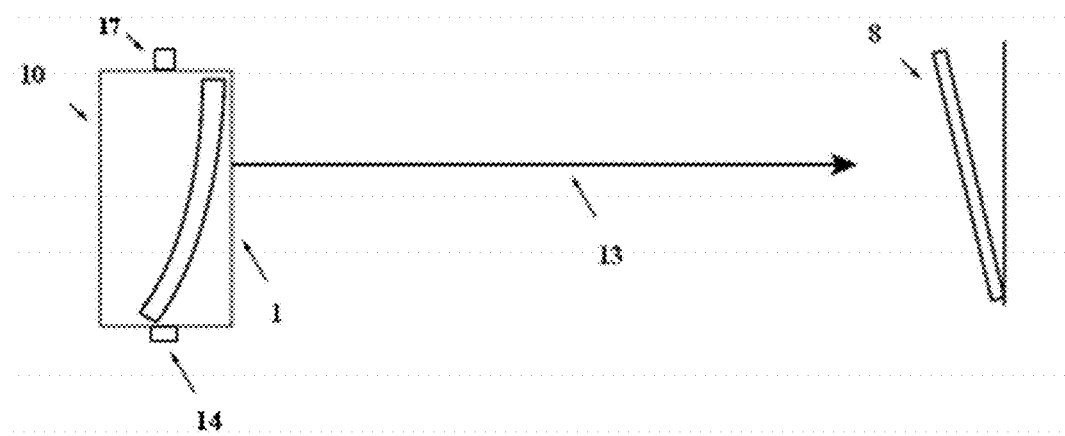
FIG. 6 shows the reflector in the line of sight of the beam detector in a NEMA 6P enclosure
Figure 7:
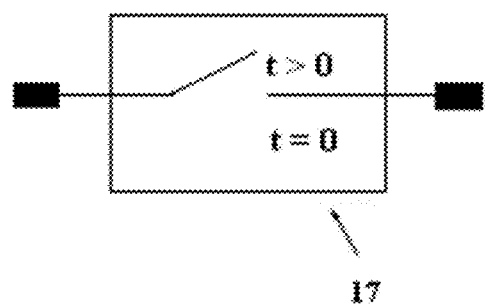
FIG. 7 shows a reset switch which is used locally to reset smoke alarm from the device

On FIG. 3, element 9 is one of the four screws that need to be in place in order to guarantee that FIG. 3 is submersible in water. Element 11 is that latch used for keeping FIG. 3 closed while 12 is used for mounting and 13 is the hinge that allows for swinging 16 which is the transparent lid. In FIG. 4, element 16 is a transparent lid with index of refraction around 1.5 to minimize the reflection of the beam emanation from 1. FIG. 6 shows element 1, the laser beam detector in 10, the enclosure in which the laser beam 15 is generated in line of sight from 8, the reflector. FIG. 6 shows the invention perspective view of the installation in the field.

The invention claimed is:

1. A smoke device for detecting smoke comprising:
a laser beam transmitter for transmitting a laser beam;
a reflecting panel that reflects the laser beam, wherein the reflecting panel is a reflector;
a laser beam detector;
wherein the laser beam detector is attached to the laser beam transmitter and the laser beam detector for detecting the ratio of the transmitted to reflected beam in order to detect any smoke obstruction in the direct path of the laser beam transmitter and the reflector; and wherein the laser beam transmitter and the laser beam detector of the smoke device are placed in a UV and protective polycarbonate enclosure that has a transparent lid and a water tight cord grip for remote alarm cable pathway and submersible in up to six feet of water for up to twenty four hours and still have its smoke detector device functions activated.

\* \* \* \* \*